United States Patent
Kishimoto et al.

(10) Patent No.: US 9,371,438 B2
(45) Date of Patent: Jun. 21, 2016

(54) HIGH MELTING POINT FLAME RETARDANT CRYSTAL AND METHOD FOR MANUFACTURING THE SAME, EPOXY RESIN COMPOSITION CONTAINING THE FLAME RETARDANT, AND PREPREG AND FLAME RETARDANT LAMINATE USING THE COMPOSITION

(75) Inventors: Daishiro Kishimoto, Osaka (JP); Yoichi Umeki, Osaka (JP)

(73) Assignee: SANKO CO., LTD., Kurume (JP)

( * ) Notice: Subject to any disclaimer, the term of this patent is extended or adjusted under 35 U.S.C. 154(b) by 724 days.

(21) Appl. No.: 13/587,067

(22) Filed: Aug. 16, 2012

(65) Prior Publication Data
US 2013/0053473 A1 Feb. 28, 2013

(30) Foreign Application Priority Data
Aug. 23, 2011 (JP) .................. 2011-181435

(51) Int. Cl.
C08K 5/5313 (2006.01)
C07F 9/6571 (2006.01)
C08J 5/24 (2006.01)
B32B 5/26 (2006.01)
B32B 15/14 (2006.01)

(52) U.S. Cl.
CPC ............... C08K 5/5313 (2013.01); B32B 5/26 (2013.01); B32B 15/14 (2013.01); C07F 9/65717 2 (2013.01); C08J 5/24 (2013.01); B32B 2260/023 (2013.01); B32B 2260/046 (2013.01); B32B 2262/101 (2013.01); B32B 2305/076 (2013.01); B32B 2307/3065 (2013.01); C08J 2363/00 (2013.01)

(58) Field of Classification Search
CPC ............................. C08L 63/00; C08K 5/5313
USPC ........................................................ 523/451
See application file for complete search history.

(56) References Cited

U.S. PATENT DOCUMENTS

| | | | |
|---|---|---|---|
| 6,291,626 B1 * | 9/2001 | Wang et al. ...................... 528/99 |
| 6,403,690 B1 * | 6/2002 | Komori et al. ................ 524/436 |
| 6,646,064 B2 * | 11/2003 | Wang et al. ..................... 525/523 |
| 6,762,251 B2 * | 7/2004 | Gunji et al. ..................... 525/523 |
| 7,446,160 B2 * | 11/2008 | Wang et al. ..................... 528/167 |
| 2003/0069356 A1 * | 4/2003 | Yasuda et al. .................. 525/107 |
| 2008/0131639 A1 * | 6/2008 | Yamamoto et al. .......... 428/41.7 |
| 2010/0108368 A1 * | 5/2010 | Sato et al. ...................... 174/258 |
| 2011/0218273 A1 * | 9/2011 | Thibault et al. ............... 523/435 |
| 2013/0215628 A1 * | 8/2013 | Matsuda et al. ............... 362/382 |
| 2013/0256002 A1 * | 10/2013 | Ozeki et al. ................... 174/251 |
| 2014/0107256 A1 * | 4/2014 | Su et al. ......................... 523/439 |

FOREIGN PATENT DOCUMENTS

| | | |
|---|---|---|
| JP | 04-011662 | 1/1992 |
| JP | 04-053874 | 2/1992 |
| JP | 11-279258 | 10/1999 |
| JP | 2000-309623 | 11/2000 |
| JP | 2001-151991 | 6/2001 |
| JP | 2001-302686 | * 10/2001 |
| JP | 2003-201332 | 7/2003 |

OTHER PUBLICATIONS

English machine translation of JP 2001-302686. Original Japanese document Oct. 31, 2001. Translation printed Jan. 6, 2015.*

English language translation of JP 2001-302686. Original Japanese document Oct. 31, 2001. Translation printed Jan 2015.*

* cited by examiner

*Primary Examiner* — Megan McCulley
(74) *Attorney, Agent, or Firm* — Maschoff Brennan

(57) ABSTRACT

Disclosed herein is a method of preparing a high-melting point flame retardant crystal, comprising the steps of: reacting 9,10-dihydro-9-oxa-10-phosphaphenanthrene-10-oxide with 1,4-naphthoquinone in an inert solvent having a dielectric constant of 10 or less to reduce a content of by-products, thereby obtaining a reaction composition; and dissolving the reaction composition in any one solvent selected from the group consisting of ethyleneglycol, propyleneglycol, diethyleneglycol, cyclohexanone, benzyl alcohol, acetate ester, benzoate ester and a mixture thereof to recrystallize and refine the reaction composition, thereby obtaining high-melting point retardant crystal, represented by Formula 1, having a start melting point of 280° C. or more and a melting point of 291° C. or more, which are measured by differential thermogravimetric analysis.

5 Claims, 2 Drawing Sheets

HIGH MELTING POINT FLAME RETARDANT CRYSTAL AND METHOD FOR MANUFACTURING THE SAME, EPOXY RESIN COMPOSITION CONTAINING THE FLAME RETARDANT, AND PREPREG AND FLAME RETARDANT LAMINATE USING THE COMPOSITION

CROSS REFERENCE TO RELATED APPLICATION

This application claims the benefit of Japanese Patent Application No. JP 2011-181435, filed Aug. 23, 2011, which is hereby incorporated by reference in its entirety into this application.

BACKGROUND OF THE INVENTION

1. Technical Field

The present invention relates to a high-melting point flame retardant crystal and method of preparing the same, a flame retardant-containing epoxy resin composition having excellent heat resistance and high-temperature reliability and having low moisture absorption and low water absorbency, a prepreg using the composition, and a flame-retardant laminate using the prepreg. More particularly, the present invention relates to an epoxy resin composition containing an additive such as a curing agent, the composition being prepared by dispersing flame retardant powder, having a start melting point of 280° C. or more and a melting point of 291° C. or more and having reactivity to epoxy resin, in uncured epoxy resin such that the flame retardant powder does not react with the uncured epoxy resin, a prepreg obtained using the composition, and a flame-retardant laminate obtained by thermally pressing the composition to cure the composition and simultaneously fixing a flame retardant.

2. Description of the Related Art

Epoxy resins have been used as an electrical insulating material because they have excellent electrical characteristics. Particularly, epoxy resins are used to manufacture laminates and printed substrates.

Although a printed substrate is provided with parts, such as LSI, IC and the like, connected and fixed by soldering, when conventional solder including lead is used, the environmental friendliness cannot be improved. For this reason, it is necessary to use lead-free solder having a melting point higher than conventional solder, so that a laminate also requires higher heat resistance and improved reliability such that it can cope with high-temperature soldering.

Further, in order to manufacture small-size high-performance electric and electronic appliances, for example, mobile phones, it is required to dispose wiring on a laminate at narrow intervals and to increase the density of the wiring. Therefore, it is necessary to increase the heat resistance of the laminate and decrease the linear expansion coefficient thereof even for the purpose of preventing a substrate from cracking or preventing wiring from being severed by thermal expansion at high temperature.

Further, since a high-density printed substrate is easily negatively affected by foreign matter such as moisture in the air, it is necessary to increase the long-term reliability and to keep the invasion of foreign matter to a minimum.

A printed substrate is provided with minute and complicated electric wiring, and is treated with a flame retardant in order to prevent a fire from breaking out because of a short or the like.

Conventionally, as laminates for printed substrates, laminates manufactured using an epoxy resin flame-retarded by a bromine compound have been generally used, but, recently, laminates using a phosphorus-based flame retardant have also been used. It is known that a phosphorus-based flame retardant has high thermal stability and contributes to the reduction in weight of a laminate compared to a bromine-based flame retardant.

Patent documents 2~6 disclose epoxy resins using a phosphorus-based flame retardant.

Patent documents 2~5 disclose methods of manufacturing a laminate using a flam-retardant epoxy resin obtained by reacting an organic phosphorus-based flame retardant with an epoxy resin. In these methods, since the solubility of the flame-retardant epoxy resin in a solvent is improved, uniform varnish can be maintained, so that the flame-retardant epoxy resin is easily impregnated in a substrate made of glass fiber or the like.

However, the solubility of the flame-retardant epoxy resin in a solvent is improved, but there is a problem that a prepreg or laminate manufactured using the flame-retardant epoxy resin is easily affected by the invasion of moisture because the organic phosphorus-based flame retardant reacting with an epoxy resin has a noncrystalline structure.

Patent document 5 discloses a flame retardant (Patent document 1) having the same molecular structure as that of the flame retardant used in the present invention. The flame retardant disclosed in patent document 5 has a start melting point of less than 280° C. and a melting point of less than 291° C., which were measured by differential thermogravimetric analysis. When a laminate is formed using the flame retardant, the flame retardant entirely reacts with an epoxy resin to lose crystallinity, so that the noncrystallized flame retardant is easily affected by the invasion of foreign matter such as moisture or the like, with the result that it is difficult to obtain heat resistance and high-temperature reliability required to cope with lead-free solder.

Further, Patent document 6 discloses a technology for improving the working efficiency by dispersing an unreacted organic phosphorus-based flame retardant in varnish.

However, even when this technology is used, since the melting point of the flame retardant is less than 265° C. at which solder resists heat, this flame retardant cannot maintain its crystalline structure to be melted at a temperature of lower than 265° C., so that its heat resistance and high-temperature reliability are not yet satisfactory.

CITED REFERENCES

Patent Documents

Japanese Unexamined Patent Application Publication (Translation of PCT Application) No. 04-53874
Japanese Unexamined Patent Application Publication No. 04-11662
Japanese Unexamined Patent Application Publication No. 11-279258
Japanese Unexamined Patent Application Publication No. 2000-309623
Japanese Unexamined Patent Application Publication No. 2001-151991
Japanese Unexamined Patent Application Publication No. 2003-201332

SUMMARY OF THE INVENTION

Accordingly, the present invention has been devised to solve the above-mentioned problems, and an object of the present invention is to provide a flame retardant-containing epoxy resin composition having excellent heat resistance and high-temperature reliability and having a low linear expansion coefficient, which can prevent a printed substrate from cracking and breaking because of thermal expansion at high temperature even when various kinds of parts are attached onto ultrafine and highly-dense wiring of the printed substrate fabricated by processing a laminate, and which has very low moisture absorption and waster absorbency such that it is not affected by moisture, electrolytes or the like even when it is used for a long period of time, and to provide a prepreg using the composition and a flame-retardant laminate using the composition.

The present inventors made an effort to accomplish the above object. As a result, they found that the formation of impurities can be prevented by lowering the dielectric constant of a solvent reacting with a flame retardant easily accommodating impurities or solvent in the molecules thereof, that the start melting point and melting point of the flame retardant can be increased by recystallizing and refining the flame retardant by using a specific solvent that reacts only with difficulty with the flame retardant, and that an epoxy resin composition constituting a prepreg using the flame retardant crystal can maintain the crystal structure of the flame retardant even when an epoxy resin and a flame retardant having a specific melting point coexist in an unreacted state, so that the epoxy resin reacts with the surface of the specific organic phosphorus-based flame retardant by thermal pressing to form a laminate, thereby fixing the flame retardant crystal in the epoxy resin. Based on these findings, the present invention was completed.

A flame retardant, which is a kind of impurity, is a factor deteriorating the inherent performance of the physical strength of an epoxy resin. Therefore, in the field of printed substrates, research into imparting a substrate with flame retardancy and preventing the deterioration of the physical properties of the substrate is ongoing. It is known in Patent document 3 and Patent document 5 that an epoxy resin substrate imparted with flame retardancy by an organic phosphorus-based flame retardant has high pyrolysis temperature and improved thermal stability compared to a conventional epoxy resin substrate imparted with flame retardancy by bromine. Further, it is proposed in Patent document 6 that an epoxy resin substrate is reformed in order to improve the working efficiency. However, under severe conditions, an epoxy resin is affected by a flame retardant, thus deteriorating the physical properties of the epoxy resin.

The present inventors have determined the causes of the deterioration of physical properties of an epoxy resin. The causes thereof are that the crystalline structure of the flame retardant is changed into a noncrystalline structure by previously reacting a flame retardant with an epoxy resin to form a polymer, that the flame retardant is melted at the time of soldering because the start melting point and melting point thereof are lower than the soldering temperature and that impurities, such as moisture and the like, easily permeate into the flame retardant crystals because the flame retardant crystals do not align regularly and densely because of the influence of impurities even when the melting point thereof is higher than the soldering temperature.

In order to accomplish the above object, an aspect of the present invention provides a method of preparing a high-melting point flame retardant crystal, comprising the steps of reacting 9,10-dihydro-9-oxa-10-phosphaphenanthrene-10-oxide with 1,4-naphthoquinone in an inert solvent having a dielectric constant of 10 or less to reduce a content of by-products, thereby obtaining a reaction composition; and dissolving the reaction composition in any one solvent selected from the group consisting of ethyleneglycol, propyleneglycol, diethyleneglycol, cyclohexanone, benzyl alcohol, acetate ester, benzoate ester and mixtures thereof to recrystallize and refine the reaction composition, thereby obtaining high-melting retardant crystal, represented by Formula 1 below, having a start melting point of 280° C. or more and a melting point of 291° C. or more, which are measured by differential thermogravimetric analysis:

[Formula 1]

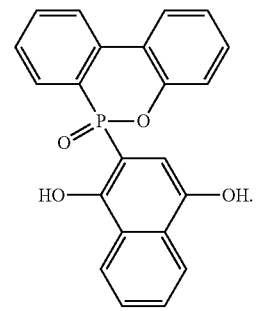

Another aspect of the present invention provides a high-melting point flame retardant crystal, prepared by the method, wherein the high-melting point flame retardant crystal is represented by Formula 1 below:

[Formula 1]

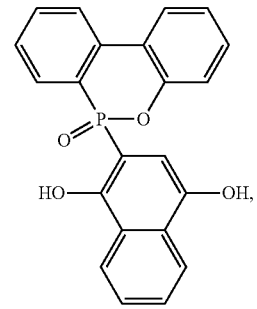

and has a start melting point of 280° C. or more and a melting point of 291° C. or more, which are measured by differential thermogravimetric analysis.

Still another aspect of the present invention provides a flame retardant-containing epoxy resin composition, obtained by dispersing flame retardant powder fowled of the high-melting point flame retardant crystal in an uncured epoxy resin in an amount of 1~35 parts by mass based on 100 parts by mass of a total solid content such that the flame retardant powder does not react with the uncured epoxy resin.

Still another aspect of the present invention provides a prepreg, formed in the shape of film or plate using flame retardant-containing epoxy resin composition.

Still another aspect of the present invention provides a flame-retardant laminate, manufactured by overlapping the film-shape or plate-shape prepreg with a substrate and then thermally pressing them to integrate the prepreg with the substrate.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
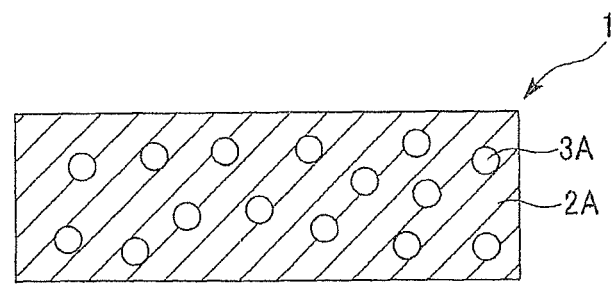
FIG. 1 is a schematic view showing flame retardant powder dispersed in a flame retardant-containing epoxy resin composition and a prepreg, wherein the flame retardant powder is formed of high-purity HCA=NQ crystal.

Hereinafter, preferred embodiments of the present invention will be described in detail with reference to the attached drawings.

(High-Melting Point Flame Retardant Crystal)

The high-melting point flame retardant crystal (hereinafter, referred to as "a flame retardant") related to the present invention is 9-hydro-10-[2-(1,4-dihydroxynaphthyl)]-9-oxa-10-phosphaphenanthrene-10-oxide (hereinafter, referred to as "HCA=NQ") represented by the following Formula 1:

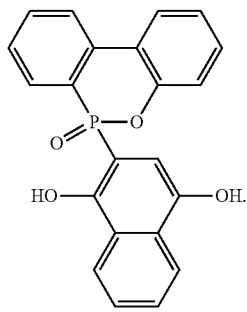

Particularly, the high-melting point flame retardant crystal is a high-purity crystal (hereinafter, referred to as "high-purity HCA=NQ crystal") having a start melting point of 280° C. or more and a melting point of 291° C. or more, which are measured by differential thermogravimetric analysis.

In the present invention, the term "start melting point measured by differential thermogravimetric analysis" is defined as an intersection point between an endothermic peak line and tangent line thereof, which are obtained by setting a sample in a differential thermogravimetric analyzer (DTG-60, manufactured by Shimadzu Corpoaration) and then performing differential thermogravimetric analysis at a heating rate of 10° C./min. Further, the term "melting point" is defined as a temperature at the lowermost portion of an endothermic peak.

Since the molecular structure of the high-purity HCA NQ crystals of the present invention is aligned regularly and densely, when an epoxy resin is mixed with this flame retardant and formed into a laminate, the epoxy resin exhibits an excellent effect of the laminate preventing the invasion of foreign matter compared to an epoxy resin mixed with a flame retardant having a noncrystalline structure or an epoxy resin mixed with a low-melting flame retardant. Therefore, in order to prevent the invasion of foreign matter such as moisture or the like, if possible, the flame retardant in the laminate may be maintained in a crystal state by using a high-melting point flame retardant.

A crystalline compound has a specific melting point depending on the kind, content and crystal structure of impurities or isomers, and its thermal expansion coefficient increases by an extreme amount after it is melted compared to before it is melted.

Further, when the content of impurities or isomer in the flame retardant crystal increases, the start melting point and melting point of the flame retardant are lowered, and thus the temperature difference therebetween becomes large. Even though a flame retardant having only a melting point is used, when the start melting point thereof is lowered by the content of impurities or the like, a printed substrate is easily cracked by thermal expansion at high temperature when various kinds of parts are attached onto the ultrafine and highly-dense wiring of the printed substrate.

Meanwhile, when the purity of the flame retardant crystal is high, both the start melting point and melting point thereof become high, and the temperature difference therebetween becomes small. Therefore, even when a various kinds of parts are attached onto an ultrafine and highly-dense wiring of the printed substrate using lead-free solder, the printed substrate does not easily crack and break because of thermal expansion at high temperature. Further, since impurities function to break down the crystal structure of molecules, foreign matter, such as moisture or the like, easily invades the printed substrate.

Therefore, it is preferred that the flame retardant that is used have a high melting point and be of high purity and that its crystal be densely aligned. Specifically, a flame retardant having a start melting point of 280° C. or more and a melting point of 291° C. or more is suitably used. In contrast, a flame retardant having a start melting point of less than 280° C. and a melting point of less than 291° C. is not greatly effective in the preventing a substrate from being invaded by foreign matter, as described above. It was ascertained that flame retardant powder formed of high-purity HCA=NQ crystal represented by Formula 1 above is suitable as the flame retardant satisfying these conditions.

When the flame retardant powder formed of high-purity HCA=NQ crystal is thermally pressed in a state in which it is dispersed in an epoxy resin film or a plate-shaped prepreg, the surface of the high-purity HCA=NQ crystal reacts with an epoxy resin to be fixed in the epoxy resin film or plate-shaped prepreg. Therefore, a flame retardant and an epoxy resin are chemically bonded with each other to prevent the deterioration of other physical properties, such as strength and the like, required for a laminate. Further, since the temperature of the flame retardant crystal dispersed in the laminate is higher than the soldering temperature, the problem of thermal expansion or swelling due to local melting at the soldering temperature does not occur.

In the present invention, a high purity HCA=NQ crystal having a start melting point of 292° C. and a melting point of 295° C. and a commercially available flame retardant [9-hydro-10-[2-(1,4-dihydroxynaphthyl)]-9-oxa-10-phosphaphenanthrene-10-oxide (brand name: HCA-HQ, manufactured by Sanko Metal Industrial Co., Ltd.)] having a start melting point of 246° C. and a melting point of 250° C. were respectively mixed with an epoxy resin, a curing agent and the like, processed into laminates and then compared with each other.

As a result, the water absorbency of the laminate fabricated using the high purity HCA=NQ crystal having a melting point of 295° C. was reduced by about 15%, and a problem of the laminate being swelled by thermal expansion was not observed even in the soldering test at 265° C. In contrast, in the laminate fabricated using the HCA-HQ having a melting point of 250° C., appearance change, such as the swelling attributable to thermal expansion during soldering, and the interlayer peeling of a part of the laminate were observed.

Comparing the laminate fabricated using the high purity HCA=NQ crystal of the present invention with a laminate fabricated using a flame retardant having a start melting point and a melting point lower than soldering temperature (265° C.), the water absorbency of the laminate fabricated using the high purity HCA=NQ crystal of the present invention became low, and the heat resistance thereof was improved. In the laminate fabricated using the high purity HCA=NQ crystal of the present invention, on one side of the laminate, the crystal region did not melt even at soldering temperature, and thus a problem of swelling accompanied by thermal expansion did not occur, but, on the other side thereof, the crystal region melted to cause thermal expansion, so that there were changes in appearance, such as swelling, interlayer peeling or the like. Particularly, it was observed that, when the flame retardant of the present invention was used, the heat resistance of the laminate was remarkably improved and there was a remarkable reduction in thermal expansion.

Further, a high purity HCA=NQ crystal having a start melting point of 292° C. and a melting point of 295° C. and a commercially available flame retardant (brand name: HCA-NQ (hereinafter, referred to as "general-purpose HCA=NQ"), manufactured by Sanko Metal Industrial Co., Ltd.) having a start melting point of 277° C. and a melting point of 290° C. were respectively mixed with an epoxy resin, a curing agent and the like, processed into laminates, and then compared with each other.

As a result, the water absorbency of the laminate fabricated using the high purity HCA=NQ crystal having a melting point of 295° C. was reduced by about 15%, and the problem of the laminate swelling because of the volatilization of absorbed water was not observed even in a soldering test conducted at 265° C. In contrast, in the laminate fabricated using the general-purpose HCA=NQ having a melting point of 290° C., there were observed changes in appearance, such as swelling attributable to the volatilization of absorbed water during soldering, and the interlayer peeling of a part of the laminate.

Comparing the laminate fabricated using the high purity HCA=NQ crystal of the present invention with a laminate fabricated using the flame retardant (general-purpose HCA=NQ), the water absorbency of the laminate fabricated using the high purity HCA=NQ crystal of the present invention became low, and the heat resistance thereof was improved. In the laminate fabricated using the high purity HCA=NQ crystal of the present invention, on one side of the laminate, a problem of swelling accompanied by moisture absorption did not occur, but, on the other side thereof, the crystal region melted to cause thermal expansion, thus causing a change in appearance, such as swelling, interlayer peeling or the like. Particularly, it was observed that, when the flame retardant of the present invention was used, the invasion of foreign matter was remarkably prevented.

Further, a laminate fabricated using high-density HCA=NQ crystal powder and an epoxy resin in an unreacted state was compared to a laminate fabricated by previously reacting high-density HCA=NQ crystal powder with an epoxy resin to make the powder noncrystalline. As a result, the water absorbency of the laminate in which the high purity HCA=NQ crystal is maintained in a crystalline state was reduced by about 24%, and the problem of the laminate swelling because of water absorption or thermal expansion was not observed even in the soldering test. In contrast, in the laminate fabricated by previously reacting high-density HCA=NQ crystal powder with an epoxy resin, there were changes in appearance, such as swelling attributable to water absorption or thermal expansion during soldering, and the interlayer peeling of a part of the laminate.

A laminate fabricated by dispersing high-density HCA=NQ crystal powder in an epoxy resin in a crystalline state was compared with a laminate fabricated by previously reacting high-density HCA=NQ crystal powder with an epoxy resin to make a noncrystalline solution. This comparison revealed a difference in water absorbency between the crystalline state and the noncrytalline state. Even here, it was ascertained that the laminate fabricated by dispersing high-density HCA=NQ crystal powder in an epoxy resin in a crystalline state is superior to the laminate fabricated by previously reacting high-density HCA=NQ crystal powder with an epoxy resin to make a noncrystalline solution.

(Method of Preparing High-Melting Flame Retardant Crystal)

The method of preparing high-melting point flame retardant crystal according to the present invention is characterized in that the high-purity HCA=NQ crystal is obtained by performing the following processes 1 and 2.

Process 1: as represented by Formula 2 below, reacting 9,10-dihydro-9-oxa-10-phosphaphenanthrene-10-oxide (a) with 1,4-naphthoquinone (b) in an inert solvent having a dielectric constant of 10 or less to reduce the content of by-products, thereby obtaining a reaction composition including the HCA=NQ (1) as a main component.

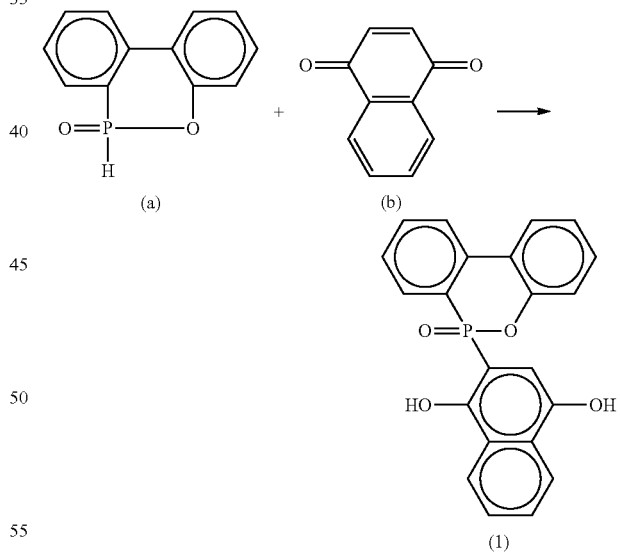

[Formula 2]

Process 2: dissolving the reaction composition obtained in the process 1 in any one solvent selected from the group consisting of ethyleneglycol, propyleneglycol, diethyleneglycol, cyclohexanone, benzyl alcohol, acetate ester, benzoate ester and mixture thereof to recrystallize and refine the reaction composition, thereby obtaining high-purity HCA NQ crystal, represented by Formula 1 above, having a start melting point of 280° C. or more and a melting point of 291° C. or more, which are measured by differential thermogravimetric analysis.

Examples of the inert solvent having a dielectric constant of 10 or less, used in process 1, may include ethyleneglycol lower alkyl ether, propyleneglycol lower alkyl ether, ethyleneglycol lower alkyl ether acetate, propyleneglycol lower alkyl ether acetate, benzene, toluene, xylene, acetate ester, benzoate ester, and the like. Among these inert solvents, acetate ester is the most preferable one.

Further, it is preferred that the reaction of process 1 be performed at a temperature of 80~140° C. for 1~12 hours.

In the method of preparing high-melting point flame retardant crystal according to the present invention, the high-purity HCA=NQ crystal, represented by Formula 1 above, having a start melting point of 280° C. or more and a melting point of 291° C. or more, which are measured by differential thermogravimetric analysis, can be efficiently prepared by performing processes 1 and 2.

(Flame Retardant-Containing Epoxy Resin Composition)

The flame retardant-containing epoxy resin composition of the present invention is obtained by dispersing flame retardant powder formed of high-purity HCA=NQ crystal in an uncured epoxy resin in an amount of 1~35 parts by mass based on 100 parts by mass of the total solid content such that the flame retardant powder does not react with the uncured epoxy resin.

Here, as the flame retardant powder formed of the high-purity HCA=NQ crystal, it is preferable to use fine crystal powder having uniform particle size for the sake of preventing an unbalance attributable to precipitation or the like or in order to fabricate a thin product such as a film or the like. Specifically, it is preferred that the average particle size of the flame retardant powder be 20 μm or less, more preferably, 0.1~5 μm. When the average particle size of the flame retardant powder is more than 20 μm, the moldability of the epoxy resin composition including the flame retardant powder becomes poor, so that it is difficult to manufacture a molded product that is thin.

This flame retardant powder formed of the high-purity HCA=NQ crystal is combined with an uncured epoxy resin in an amount of 1~35 parts by mass based on 100 parts by mass of the total solid content. When the amount of the flame retardant powder is less than 1 part by mass, the epoxy resin composition including the flame retardant powder cannot exhibit flame retardancy. Further, when the amount thereof is more than 35 parts by mass, the flame retardancy of the epoxy resin composition including the flame retardant powder cannot be further improved, and the strength thereof is remarkably reduced, which is not preferable. The optimum amount of the high-purity HCA=NQ crystal powder may be 1~25 parts by mass based on 100 parts by mass of the total solid content.

The uncured epoxy resin used in the flame retardant-containing epoxy resin composition is not particularly limited. Examples of the uncured epoxy resins may include bisphenol A type epoxy resin, bisphenol F type epoxy resin, phenol novolac type epoxy resin, cresol novolac type epoxy resin, phenoxy resin, and phosphorus-modified epoxy resin. These epoxy resins may be used independently or in combination.

The flame-retardant epoxy resin composition of the present invention is processed into a desired molded product using a curing agent. Here, the curing agent is not particularly limited as long as it is a commonly-used curing agent for epoxy resin. Examples of the curing agents may include amines such as diaminodiphenylmethane, dicyandiamide and the like, polyamine resins, polyamide resins, polyamide-imide resins, phenol novolac resin having two or more phenolic hydroxyl groups, cresol novolac resin, bisphenol novolac resin, melamine-modified phenol novolac resin, reaction products of phenol and triazine, benzoxazine compounds, glyoxal phenol polycondensates, phosphorus-modified phenol derivatives, phosphorus-modified bisphenol derivatives, acid anhydrides, and the like. These curing agents may be used independently or in combination.

The flame-retardant epoxy resin composition of the present invention may further include a curing accelerator in order to accelerate the curing of the composition. This curing accelerator is not particularly limited. As the curing accelerator, commonly-used various kinds of curing accelerators, for example, acid anhydrides, polyamine compounds and phenol compounds, may be used. These curing accelerators may be used independently or in combination thereof.

The flame-retardant epoxy resin composition of the present invention may further include other additives, besides the above additives. Specific examples of the additives may include, but are not limited to, inorganic fillers such as aluminum hydroxide, magnesium hydroxide, silica and the like, flame retarding agents such as inorganic molybdenum compounds, inorganic titanium compounds and the like, and organic rubbers such as polyvinyl acetal resin, SBR, BR, butyl rubber, butadiene-acrylonitrile copolymer rubber and the like.

In the flame-retardant epoxy resin composition of the present invention, in order to obtain a desired molded product by uniformly mixing and dispersing the above-mentioned raw materials, a single solvent or mixed solvent may be used. This solvent is not particularly limited as long as it is suitable for attaining the purpose. Specific examples of the solvents may include toluene, xylene, methyl ethyl ketone, dimethylformamide, methoxypropanol, propanol, butanol, and the like.

The flame-retardant epoxy resin composition of the present invention is formed into vanish for preparing a prepreg by using flame retardant powder formed of high-purity HCA=NQ crystal, an epoxy resin, and a curing agent as essential components and, if necessary, suitably combining them with other additives.

Since the flame retardant-containing epoxy resin composition of the present invention is prepared by dispersing high-purity HCA=NQ crystal powder in an uncured epoxy resin in an amount of 1~35 parts by mass based on 100 parts by mass of the total solid content such that the flame retardant powder does not react with the uncured epoxy resin, the melting point of the high-purity HCA=NQ crystal powder is higher than the soldering temperature, so that the crystal structure of the high-purity HCA=NQ crystal powder is maintained even when soldering is conducted using lead-free solder, with the result that the substrate fabricated using the composition does not crack nor break as a result of thermal expansion at high temperature, and is not easily affected by moisture, electrolytes or the like even when used for a long period of time.

(Prepreg)

The prepreg of the present invention includes the flame retardant-containing epoxy resin composition, and is prepared in the form of a film or plate.

FIG. 1 is a schematic view showing an example of a prepreg according to the present invention. As shown in FIG. 1, the prepreg 1 is configured such that flame retardant powder 3A having high-purity HCA=NQ crystal is dispersed in an uncured epoxy resin 2A. The flame retardant powder 3A dispersed in the uncured epoxy resin 2A is maintained in a crystal state without being melted.

The prepreg of the present invention can be prepared using the flame retardant-containing epoxy resin composition. For example, preferably, the prepreg may be prepared by using flame retardant powder farmed of high-purity HCA=NQ crystal, an epoxy resin, and a curing agent as essential components and, if necessary, suitably combining them with other additives to obtain a varnish for preparing the prepreg, and impregnating a substrate such as a glass cloth with the obtained varnish, and then drying the substrate impregnated with the varnish. The thickness and quality of this prepreg are not particularly limited.

Since the prepreg of the present invention is obtained in the form of a film or plate using the flame retardant-containing epoxy resin composition, the melting point of the flame retardant is higher than the soldering temperature, so that the crystal structure of the high-purity HCA=NQ crystal powder is maintained even when soldering is conducted using lead-free solder, with the result that the substrate fabricated using the composition does not crack nor break as a result of thermal expansion at high temperature, and is not easily affected by moisture, electrolyte or the like even when it is used for a long period of time.

(Flame-Retardant Laminate)

The flame-retardant laminate of the present invention is manufactured by overlapping the film-shape or plate-shape prepreg with a substrate and then thermally pressing them to integrate the prepreg with the substrate.

As the substrate, copper foil, a synthetic resin film, a copper clad laminate of copper foil and a resin layer, a copper clad laminate provided with a circuit, or the like may be used.

Figure 2:
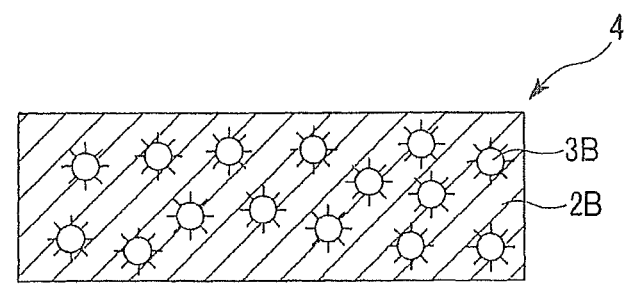
FIG. 2 is a schematic view showing flame retardant powder dispersed in a flame-retardant laminate, wherein the flame retardant powder is formed of an epoxy resin and high-purity HCA=NQ crystal and the surface of the flame retardant powder is bonded with an epoxy resin.

FIG. 2 is a schematic view showing epoxy resin and flame retardant powder dispersed in a flame-retardant laminate of according to the present invention. The flame-retardant laminate of the present invention includes a flame retardant-containing epoxy resin layer 4. In the flame retardant-containing epoxy resin layer 4, flame retardant powder 3B formed of high-purity HCA=NQ crystal is dispersed in an epoxy resin 2B, and the surface of the flame retardant powder 3B is bonded with the epoxy resin 2B.

The flame-retardant laminate of the present invention is manufactured by overlapping the prepreg with a substrate such as copper foil or a copper clad laminate and then thermally pressing them to integrate the prepreg with the substrate. In this case, the flame retardant-containing epoxy resin composition in the prepreg is cured by thermal pressing, and simultaneously the surface of the flame retardant powder 3B reacts with the epoxy resin 2B so that they are bonded and fixed to each other.

In the flame-retardant laminate of the present invention, the flame retardant-containing epoxy resin layer 4 may be formed of one or more layers. The kind and number of sheets of another substrate such as copper foil, a synthetic resin or the like which is laminated, and the number of layers of the flame retardant-containing epoxy resin layer 4 are not particularly limited.

The flame-retardant laminate of the present invention is manufactured by overlapping the film-shape or plate-shape prepreg with a substrate and then thermally pressing them to integrate the prepreg with the substrate. As a result, a printed substrate manufactured by processing the flame-retardant laminate does not crack nor break because of thermal expansion at high temperature even when various kinds of parts are attached onto the ultrafine and highly-dense wiring of the printed substrate, and the printed substrate has very low moisture absorption and waster absorbency such that it is not influenced by moisture, electrolyte or the like even when it is used for a long period of time, thereby obtaining a flame-retardant laminate having excellent heat resistance and high-temperature reliability and having a low linear expansion coefficient.

EXAMPLES

Hereinafter, the present invention will be described in more detail with reference to the following Examples and Comparative Examples. However, the scope of the present invention is not limited to these Examples.

In the Examples, the evaluation of physical properties of each laminate was performed as follows.

Boiling water absorbency (%) was evaluated after immersing each laminate in boiling water at 100° C. for 2 hours. Boiling water absorbency=(mass of laminate after absorbing water−mass of laminate before absorbing water)/mass of laminate before absorbing water×100.

Heat resistance of laminate to boiling solder was evaluated by observing changes in appearance, such as swelling or the like, of a laminate with the naked eye after immersing each laminate in 100° C. boiling water for 6 hours and then further immersing the laminate in a 265° C. solder bath for 20 seconds.

Example 1

Process 1:

1296 g of 9,10-dihydro-9-oxa-10-phosphaphenanthrene-10-oxide (HCA, manufactured by Sanko Metal Industrial Co., Ltd.) and 3888 g of benzyl acetate were put into a 10 L four-neck flask, and a reactor was provided with a thermometer, a dropping funnel and a condenser.

The reactor was filled with nitrogen gas and sealed, and then stirring and heating was started under a nitrogen atmosphere. When the temperature in the reactor reached 100° C., a solution, in which 948 g of 1,4-naphthoquinone had been previously dissolved in 2844 g of benzyl acetate, was completely introduced into the reactor by the dropping funnel over 8 hours while maintaining the temperature in the reactor at 100° C. Then, the product of the reaction was aged for 4 hours under the same conditions, cooled to 25° C. and then filtered to obtain 2625 g of a reaction composition.

Process 2:

2625 g of the reaction composition obtained in the process 1 and 13125 g of benzyl acetate were put into a 20 L four-neck flask, and then recrystallized and refined to obtain 1997 g of high-purity HCA=NQ crystal which is white crystalline powder. The yield thereof was 89.0%, the start melting point thereof was 292° C., and the melting point thereof was 295° C.

Example 2

25 parts by mass of the high-purity HCA=NQ crystal (start melting point 292° C., melting point 295° C.) prepared in Example 1, 75 parts by mass of bisphenol A type epoxy resin (EPICOT 1001, manufactured by Nippon Epoxy Resin Co., Ltd.), 20 parts by mass of phenol novolac epoxy resin (DEN438, manufactured by Dow Chemical Japan Ltd.), 3 parts by mass of dicyandiamide, 45 parts by mass of aluminum hydroxide, 0.3 parts by mass of 2-ethyl-4-methylimidazole and 72 parts by mass of methyl ethyl ketone were uniformly mixed to obtain varnish.

Subsequently, a glass cloth having a thickness of 0.18 mm was impregnated with the obtained varnish, and then heated to 150° C. for 5 minutes to prepare a prepreg. These four prepregs were overlapped to form a prepreg assembly, both sides of the prepreg assembly were covered with copper foil having a thickness of 18 μm, and then the prepreg assembly was thermally pressed at a temperature of 180° C. and a pressure of 2.5 MPa for 90 minutes to obtain a copper clad laminate.

The obtained copper clad laminate was etched to remove copper therefrom, and then the boiling water absorbency, heat resistance to boiling solder and flame retardancy of the laminate were evaluated. As a result, the boiling water absorbency thereof was 0.60%, and there were observed no changes in appearance thereof, such as swelling or the like, accompanied by thermal expansion in the heat resistance test to boiling solder. Further, in the UL-94 burning test, the voltage (V) was 0.

Example 3

25 parts by mass of the high-purity HCA=NQ crystal (start melting point 292° C., melting point 295° C.) prepared in Example 1, 75 parts by mass of cresol novolac epoxy resin (N-673, manufactured by DIC Co., Ltd.), 24 parts by mass of phenol novolac resin (PSM6200, manufactured by Gunei Chemical Industry Co., Ltd.), 1 part by mass of glyoxal phenol polycondensate (Durite SD-375B, manufactured by Boden Chemical Co. Ltd.), 45 parts by mass of aluminum hydroxide, 0.3 parts by mass of 2-ethyl-4-methylimidazole and 72 parts by mass of methyl ethyl ketone were uniformly mixed to obtain a varnish.

Subsequently, a glass cloth having a thickness of 0.18 mm was impregnated with the obtained varnish, and then heated to 150° C. for 5 minutes to prepare a prepreg. These four prepregs were overlapped to form a prepreg assembly, both sides of the prepreg assembly were covered with copper foil having a thickness of 18 μm, and then the prepreg assembly was thermally pressed at a temperature of 180° C. and a pressure of 2.5 MPa for 90 minutes to obtain a copper clad laminate.

The obtained copper clad laminate was etched to remove copper therefrom, and then the boiling water absorbency, heat resistance to boiling solder and flame retardancy of the laminate were evaluated. As a result, the boiling water absorbency thereof was 0.40%, and the changes in appearance thereof, such as swelling or the like, accompanied by thermal expansion in the heat resistance test to boiling solder, were not observed. Further, in the UL-94 burning test, the voltage (V) was 0.

Example 4

A copper clad laminate was obtained in the same manner as in Example 2, except that 55 parts by mass (37% based on total solid content of resin) of high-purity HCA=NQ crystal was used.

The obtained copper clad laminate was etched to remove copper therefrom, and then the boiling water absorbency, heat resistance to boiling solder and flame retardancy of the laminate were evaluated. As a result, the boiling water absorbency thereof was 0.63%, and the appearance change thereof, such as swelling or the like, accompanied by thermal expansion in the heat resistance test to boiling solder was not observed, but the laminate was easily broken because its strength was low. Further, in the UL-94 burning test, the voltage (V) was 0.

Comparative Example 1

A copper clad laminate was obtained in the same manner as in Example 2, except that 25 parts by mass of commercially available 9-hydro-10-(2,5-dihydroxyphenyl)-9-oxa-10-phosphaphenanthrene-10-oxide (HCA-HQ (start meting point 246° C., melting point 250° C.), manufactured by Sanko Metal Industrial Co., Ltd.) was used as a flame retardant.

The obtained copper clad laminate was etched to remove copper therefrom, and then the boiling water absorbency, heat resistance to boiling solder and flame retardancy of the laminate were evaluated. As a result, the boiling water absorbency thereof was 0.71%, and the changes in appearance thereof, such as swelling or the like, accompanied by thermal expansion in the heat resistance test to boiling solder, were slightly observed. The swelling becomes a cause of a printed substrate cracking or breaking at high temperature when various kinds of parts are attached onto ultrafine and highly-dense wiring of the printed substrate. Therefore, swelling is not preferred. Further, in the UL-94 burning test, the voltage (V) was 0.

Comparative Example 2

25 parts by mass of the high-purity HCA=NQ crystal (9-hydro-10-[2-(1,4-dihydroxyphenyl)]-9-oxa-10-phosphaphenanthrene-10-oxide (HCA-HQ, manufactured by Sanko Metal Industrial Co., Ltd.)) prepared in Example 1 was mixed with 75 parts by mass of bisphenol A type epoxy resin (EPICOT 1001, manufactured by Nippon Epoxy Resin Co., Ltd.), 100 parts by mass of cyclohexanone (solvent) and 0.3 parts by mass of triphenylphosphine to obtain a phosphorus-modified epoxy resin.

20 parts by mass of the obtained phosphorus-modified epoxy resin was mixed with 20 parts by mass of phenol novolac epoxy resin (DEN438, manufactured by Dow Chemical Japan Ltd), 3 parts by mass of dicyandiamide, 45 parts by mass of aluminum hydroxide and 0.3 parts by mass of 2-ethyl-4-methylimidazole to obtain varnish.

The obtained copper clad laminate was etched to remove copper therefrom, and then the boiling water absorbency, heat resistance to boiling solder and flame retardancy of the laminate were evaluated. As a result, the boiling water absorbency thereof was 0.79%, and some slight changes in appearance thereof, such as swelling or the like, accompanied by minute thermal expansion in the heat resistance test to boiling solder, were observed. The swelling becomes a cause of a printed substrate cracking or breaking at high temperature when various kinds of parts are attached onto the ultrafine and highly-dense wiring of the printed substrate. Therefore, the swelling is not preferred. Further, in the UL-94 burning test, the voltage (V) was 0.

Comparative Example 3

A copper clad laminate was obtained in the same manner as in Example 2, except that 25 parts by mass of 9-hydro-10-[2-(14-dihydroxynaphthyl)]-9-oxa-10-phosphaphenanthrene-10-oxide (general purpose HCA=NQ (start meting point 277° C., melting point 290° C.), manufactured by Sanko Metal Industrial Co., Ltd.) was used as a flame retardant.

The obtained copper clad laminate was etched to remove copper therefrom, and then the boiling water absorbency, heat resistance to boiling solder and flame retardancy of the laminate were evaluated. As a result, the boiling water absorbency thereof was 0.70%, and there were slight changes in the appearance thereof, such as swelling or the like, accompanied by the volatilization of absorbed moisture in the heat resistance test to boiling solder that were observed. The swelling becomes a cause of a printed substrate cracking or breaking at high temperature when various kinds of parts are attached onto the ultrafine and highly-dense wiring of the printed substrate. Therefore, swelling is not preferred. Further, in the UL-94 burning test, the voltage (V) was 0.

Figure 3:
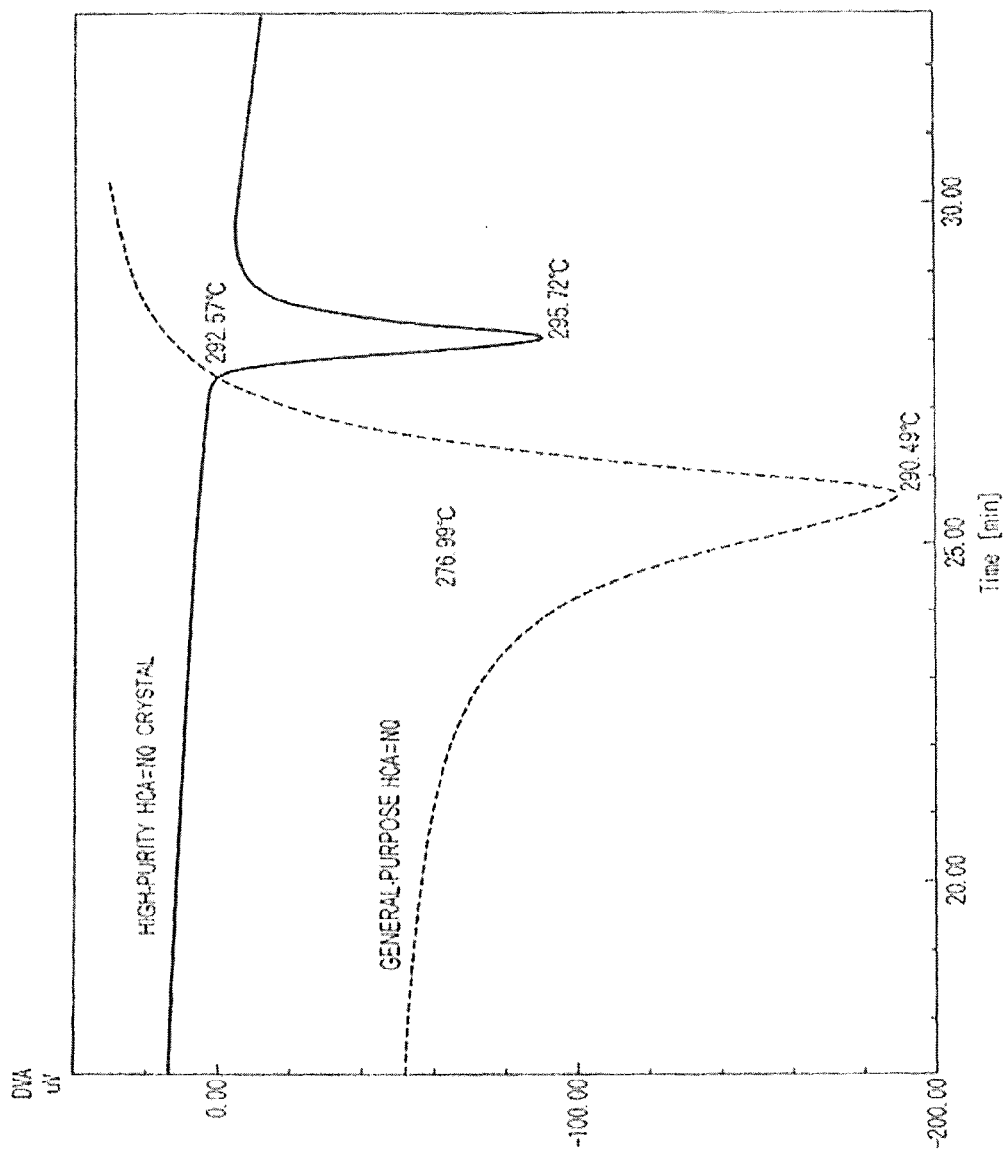
FIG. 3 is a graph showing the results of differential thermogravimetric analyses of high-purity HCA=NQ crystal prepared in the Example and commercially available HCA=NQ crystal.

FIG. 3 is a graph showing the results of differential thermogravimetric analysis of the high-purity HCA=NQ crystal prepared in Example 1 and the general-purpose HCA=NQ used in Comparative Example 3.

As shown in FIG. 3, it can be ascertained that the start melting point and melting point of the high-purity HCA=NQ crystal prepared in Example 1 become higher than those of the general-purpose HCA=NQ used in Comparative Example 3.

As described above, according to the method of preparing high-melting point flame retardant crystal of the present invention, the high-melting point flame retardant crystal, represented by Formula 1 above, having a start melting point of 280° C. or more and a melting point of 291° C. or more, as measured by differential theiniogravimetric analysis, can be efficiently prepared.

Since the melting point of the high-melting point flame retardant crystal obtained by the method is higher than the solder temperature, when flame retardant powder formed of the high-melting point flame retardant crystal is included in a resin composition, the crystal structure of the flame retardant powder maintains its form even when soldering is conducted using lead-free solder, with the result that a substrate fabricated using the composition does not crack nor break because of thermal expansion at high temperature, and is not easily affected by moisture, electrolytes or the like even when used for a long period of time.

Since the flame retardant-containing epoxy resin composition of the present invention is prepared by dispersing flame retardant powder formed of the high-melting point flame retardant crystal in an uncured epoxy resin in an amount of 1~35 parts by mass based on 100 parts by mass of the total solid content such that the flame retardant powder does not react with the uncured epoxy resin, the melting point of the flame retardant powder is higher than the soldering temperature, so that the crystal structure of the flame retardant powder is maintained even when soldering is conducted using lead-free solder, with the result that the substrate fabricated using the composition does not crack nor break because of thermal expansion at high temperature, and is not easily affected by moisture, electrolytes or the like even when used for a long period of time.

Since the prepreg of the present invention is obtained in the form of a film or plate using the flame retardant-containing epoxy resin composition, the melting point of the flame retardant powder is higher than the soldering temperature, so that the crystal structure of the flame retardant powder maintains its form even when soldering is conducted using lead-free solder, with the result that a substrate fabricated using the composition does not crack nor break because of thermal expansion at high temperature, and is not easily affected by moisture, electrolytes or the like even when used for a long period of time.

Since the flame-retardant laminate of the present invention is manufactured by overlapping the film-shape or plate-shape prepreg with a substrate and then thermally pressing them to integrate the prepreg with the substrate, a printed substrate manufactured by processing the flame-retardant laminate does not crack nor break because of thermal expansion at high temperature even when various kinds of parts, such as LSI, IC and the like, are attached onto the ultrafine and highly-dense wiring of the printed substrate, and the printed substrate has very low moisture absorption and waster absorbency such that it is not affected by moisture, electrolyte or the like even when used for a long period of time, thereby obtaining a flame-retardant laminate that has excellent heat resistance, high-temperature reliability and a low linear expansion coefficient.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of preparing a high-melting point flame retardant crystal, comprising the steps of:
   reacting 9,10-dihydro-9-oxa-10-phosphaphenanthrene-10-oxide with 1,4-naphthoquinone in an inert solvent having a dielectric constant of 10 or less to reduce a content of by-products, thereby obtaining a reaction composition; and
   dissolving the reaction composition in any one solvent selected from the group consisting of ethyleneglycol, propyleneglycol, diethyleneglycol, cyclohexanone, benzyl alcohol, acetate ester, benzoate ester and mixture thereof to recrystallize and refine the reaction composition, thereby obtaining high-melting point retardant crystal, represented by Formula 1 below, having a start melting point of 280.degree. C. or more and a melting point of 291.degree. C. or more, which are measured by differential thermogravimetric analysis:

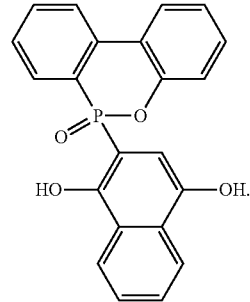 [SMILES: O=P1(c2cc(O)c3ccccc3c2O)Oc2ccccc2-c2ccccc21]

[Formula 1]

2. A high-melting point flame retardant crystal, prepared by the method of claim 1, wherein the high-melting point flame retardant crystal is represented by Formula 1 below:

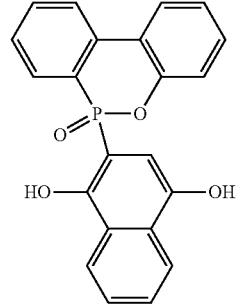

[Formula 1]

and has a start melting point of 280.degree. C. or more and a melting point of 291.degree. C. or more, which are measured by differential thermogravimetric analysis.

3. A flame retardant-containing epoxy resin composition, obtained by dispersing flame retardant powder formed of the high-melting point flame retardant crystal of claim 2 in an uncured epoxy resin in an amount of 1~35 parts by mass based on 100 parts by mass of a total solid content such that the flame retardant powder does not react with the uncured epoxy resin.

4. A prepreg in the shape of a film or a plate using the flame retardant-containing epoxy resin composition of claim 3.

5. A flame-retardant laminate, manufactured by overlapping the prepreg in the shape of a film or a plate of claim 4 with a substrate and then thermally pressing them to integrate the prepreg with the substrate.

* * * * *